United States Patent [19]

Yamashita et al.

[11] Patent Number: 5,100,789
[45] Date of Patent: Mar. 31, 1992

[54] **PROCESS FOR THE PRODUCTION OF MEVALONIC ACID BY A STRAIN OF *SACCHAROMYCOPSIS FIBULIGERA***

[75] Inventors: Haruyuki Yamashita; Hiromu Sugiyama, both of Tokyo, Japan

[73] Assignee: Ashahi Denka Kogyo Kabushiki Kaisha, Tokyo, Japan

[21] Appl. No.: 475,178

[22] Filed: Feb. 5, 1990

[30] Foreign Application Priority Data

Feb. 14, 1989 [JP] Japan ................................. 1-34607

[51] Int. Cl.$^5$ ........................... C12P 7/40; C12N 1/14
[52] U.S. Cl. .................................. 435/136; 435/254; 435/911
[58] Field of Search ...................... 435/135, 254, 911

[56] References Cited

U.S. PATENT DOCUMENTS 3,619,369  11/1971  Onishi et al. ........................ 435/158
4,410,629  10/1983  Terahara et al. .................... 435/136

FOREIGN PATENT DOCUMENTS 0281143  9/1988  European Pat. Off. .

OTHER PUBLICATIONS

Tamura et al., Applied Microbiology, 16(7), pp. 965-972, 1968.
Sigma Chemical Company, Biochemical and Organic Compounds for Research and Diagonostic Clinical Reagents, p. 440, 1985.
"Production of Extracellular Amylase by Endomycopsis fibuliger on Complex Starch Substrates", *Chemical Abstracts*, vol. 104, No. 5, No. 32994j, 1986, by J. Gasperik et al., p. 458.
"Fermentative Production of Mevalonic Acid", *Chemical Abstracts*, vol. 104, No. 7, No. 49871q, 1986, by K. Takahara et al., p. 432.

*Primary Examiner*—Douglas W. Robinson
*Assistant Examiner*—C. Geckle
*Attorney, Agent, or Firm*—Young & Thompson

[57] ABSTRACT

In the production of mevalonic acid by culturing a mevalonic acid-producing microorganism in a medium, at least peptone originating from casein and corn steep liquor are added to the medium. The content of said peptone ranges from 0.01 to 10% by weight in terms of dry matters, while that of the corn steep liquor ranges from 0.01 to 10% by weight in terms of dry matters.

5 Claims, No Drawings

PROCESS FOR THE PRODUCTION OF MEVALONIC ACID BY A STRAIN OF *SACCHAROMYCOPSIS FIBULIGERA*

BACKGROUND OF THE INVENTION

1. Field of the Invention

This invention relates to a process for the production of mevalonic acid. In particular, it relates to a process for economically producing mevalonic acid at a high yield.

It is known that mevalonic acid exists in the form of an acid and in the form of a lactone which may be readily converted into each other. Unless otherwise noted, the term "mevalonic acid" as used herein involves both of these forms.

2. Description of the Prior Art

Mevalonic acid, which was isolated by Wright et al. for the first time [cf. Journal of the American Chemical Society, 78, 5273-5275 (1956)], is known as an important intermediate in the synthesis of various isoprenoids such as cholesterol.

Further, mevalonic acid takes an important role in the metabolism in organisms. For example, it promotes the growth of various microorganisms, animals and/or plants. Therefore it is employed as a growth promoter for microorganisms, animals and plants. Furthermore, mevalonic acid is employed as a precursor for, e.g., pyrethroid agricultural chemicals, ubiquinone, dolichol and fat-soluble vitamins.

It is preferable to use natural (R-form) mevalonic acid for these purposes. However natural mevalonic acid is hardly available. Thus synthetic racemic mevalonic acid has been used hitherto.

A known process for the production of natural mevalonic acid comprises using a microorganism such as *Saccharomycopsis fibuligera* and thus accumulating mevalonic acid in a medium at a yield of 12 mg/ml at the highest (cf. Japanese Patent Laid-Open No. 216484/1988, No. 216485/1988, No. 216486/1988 and No. 216487/1988). However it has been demanded to establish a process whereby mevalonic acid can be more efficiently accumulated at a higher yield.

It is also demanded to develop a process therefor wherein inexpensive culture materials are used, since these known methods require expensive materials such as malt extract and meat extract.

SUMMARY OF THE INVENTION

It is an object of the present invention to provide a process for the production of mevalonic acid at a high yield with the use of inexpensive culture materials.

According to the present invention, the above-mentioned object can be achieved by providing a process for the production of mevalonic acid by culturing a mevalonic acid-producing microorganism in a medium, wherein said medium contains at least [A]0.01 to 10% by weight, in terms of dry matters, of peptone originating from casein and [B]0.01 to 10% by weight, in terms of dry matters, of corn steep liquor as organic nitrogen sources.

According to the process of the present invention for the production of mevalonic acid mevalonic acid can be economically obtained at a high yield.

DETAILED DESCRIPTION OF THE INVENTION

As the peptone originating from casein [A] to be used in the present invention, any one may be used so long as it originates from various caseins. For example, those obtained by hydrolyzing calcium caseinate or sodium caseinate produced from cow's milk or goat's milk with various proteases originating from animals, plants or microorganisms, such as pepsin, trypsin, pancreatin or bromelain, an acid or an alkali may be used therefor.

As the above-mentioned peptone, it is preferable to use those obtained by effecting the hydrolysis in such a manner as to regulate the amino nitrogen content in the total nitrogen content to 20 to 40% by weight, still preferably 25 to 35% by weight.

When the content of the amino nitrogen exceeds the upper limit specified above, the resulting peptone would frequently contain a large amount of impurities formed as by-products of the hydrolysis. In this case, the yield of the mevalonic acid would be lowered. When the content of the amino nitrogen is smaller than the lower limit specified above, on the other hand, the yield of the mevalonic acid would be also lowered. This might be because the resulting peptone is less available for microorganisms.

The medium contains the peptone originating from casein [A] in an amount of 0.01 to 10% by weight in the terms of dry matters.

When the content of the peptone originating from casein [A] is smaller than the lower limit specified above, the yield of the mevalonic acid cannot be elevated. When it exceeds the above-mentioned upper limit, on the other hand, the excessively large amount of the cells would cause shortage of oxygen. In the case also, the yield of the mevalonic acid cannot be elevated.

Examples of the corn steep liquor [B] to be used in the present invention are as follows:

(1) an immersion liquor obtained by immersing at least fresh and/or dry grains of so-called corn, i.e., a plant belonging to the genus Zea (Graminales, Gramineae) in warm water at 30° to 70° C., preferably 40° to 50° C., for at least 24 hours, preferably at least 48 hours.

(2) A culture medium obtained by immersing at least fresh and/or dry grains of the above-mentioned corn in warm or hot water at 30° C. or above, preferably 50° C. or above, for 5 minutes to 24 hours, preferably 1 to 12 hours and then culturing one or more lactic acid bacteria belonging to the genus, for example, Streptococcus, Lactobacillus, Pediococcus, Bifidobacterium or Leuconostoc in a conventional manner at 20° to 45° C., preferably 30° to 37° C., for 3 to 96 hours, preferably 6 to 48 hours.

The medium contains this corn steep liquor [B] in an amount of 0.01 to 10% by weight in terms of dry matters.

When the content of the corn steep liquor [B] is smaller than the lower limit specified above, the yield of the mevalonic acid cannot be elevated. When it exceeds the upper limit specified above, on the other hand, the excessively large amount of the cells would cause shortage of oxygen. In this case also, the yield of the mevalonic acid cannot be elevated.

In the present invention, mevalonic acid can be more efficiently produced by regulating the total amount of the peptone originating from casein [A] and the corn steep liquor [B] to, preferably, 0.2 to 11% by weight, still preferably 0.4 to 5% by weight.

In the present invention, the medium in which the mevalonic acid-producing microorganism is to be cultured may have the same composition as those of known ones, except that at least the above-mentioned peptone originating from casein [A] and the corn steep liquor [B] are contained therein. For example, a medium comprising 5 to 15% by weight of a carbon source such as glucose or sucrose, 0.01 to 10% by weight, in terms of dry matters, of the peptone originating from casein, 0.01 to 10% by weight, in terms of dry matters, of the corn steep liquor and water (the balance) may be used therefor.

This medium may further contain, for example, other organic nitrogen sources, surfactants such as nonionic surfactants capable of solubilizing the cell wall of the microorganism, phosphates and inorganic salts such as potassium salts, magnesium salts and calcium salts, without departing from the spirit of the present invention. The amount of each of these additives may preferably range from 0.01 to 5% by weight.

Furthermore, the medium may contain synthetic polymers and silicone antifoaming agents, without departing from the spirit of the present invention.

The mevalonic acid-producing microorganism to be used in the present invention may be any one so long as it can substantially produce mevalonic acid. For example, those described in Japanese Patent Laid-Open No. 16487/1988 such as strains belonging to *Saccharomycopsis fibuligera* may be preferably employed to thereby efficiently produce mevalonic acid.

The method for culturing said mevalonic acid-producing microorganism in said medium in the present invention is not particularly restricted but any known culture method may be employed therefor. For example, a method described in Japanese Patent Laid-Open No. 216484/1988, which comprises culturing a microorganism at 20° to 40° C., preferably 25° to 35° C., under shaking or aerating and stirring at 100 to 500 rpm, preferably 200 to 400 rpm, and at 0.2 to 1.5 VVM, preferably 0.5 to 1.0 VVM, may be preferably employed to thereby efficiently culture the microorganism.

It is further preferable that to culture the microorganism for a given period of time under shaking and/or aerating and stirring, add a medium containing a carbon source to the culture medium one or more times, and further continue the culture, thus efficiently producing mevalonic acid.

The mevalonic acid produced according to the process of the present invention may be purified in a known manner. For example, the purification may be conducted as follows. After the completion of the culture, the cells are removed from the culture medium by a known method such as centrifugation or filtration through an organic synthetic membrane such as a membrane filter. Next, the culture medium is purified by a conventional method, for example, purification with the use of a reverse osmosis membrane, silica gel, an ion exchange resin or a porous polymer resin, solvent extraction with the use of ethyl acetate or methyl ethyl ketone, distillation under reduced pressure, molecular distillation or crystallization.

To further illustrate the present invention, the following Example and Comparative Examples will be given.

In the following Example and Comparative Examples, mevalonic acid was determined by the following method.

Determination of mevalonic acid 1.0 ml of a sample was collected in a test tube and acidified by adding five or six drops of 50% (W/W) phosphoric acid.

Next, 1 g of anhydrous $Na_2SO_4$ was added thereto. 2.0 ml of ethyl acetate was further added thereto and the obtained mixture was stirred for 30 seconds.

The mixture was centrifuged in a rotator of 14 cm in radius at 2500 rpm. The upper ethyl acetate phase was introduced into another test tube A and evaporated to dryness.

To the lower aqueous phase was added 2.0 ml of ethyl acetate followed by stirring for 30 seconds.

The mixture was similarly centrifuged. The upper ethyl acetate phase was introduced into the test tube A and evaporated to dryness.

The same procedure was repeated to thereby give 6 ml, in total, of the dried ethyl acetate phase.

This dry product was dissolved in 1 ml of isopropanol containing 10 mg/ml of γ-valerolactone (a product of Aldrich Chemical Co.) as an internal standard, and subjected to high-performance liquid chromatography.

The high-performance liquid chromatography was conducted under the following condition:

column: Nucleosil 5N $(CH_3)_2$ (a product of M. Nagel., West Germany), 4.6 $\phi \times 250$ mm, 40° C.

mobil phase: n-hexane/isopropanol (9/1), 2.0 ml/min.

detector: differential refractometer.

injection: 5 μl.

EXAMPLE 1

5 ml of a medium comprising 10% by weight of glucose, 0.5% by weight, in terms of dry matters, of peptone originating from casein (amino nitrogen content: 31% by weight), 1.0% by weight (0.5% by weight in terms of dry matters) of corn steep liquor (immersion liquor, 5° C., 50 hours, containing 50% by weight of moisture), 0.1% by weight of $KH_2PO_4$, 0.05% by weight of $MgSO_4 \cdot 7H_2O$, 1.0% by weight of $CaCO_3$ and water (the balance) was introduced into a test tube [24 (diameter) ×200 mm] and sterilized at 121° C. for 15 minutes.

One platinum loopful of *Saccharomycopsis fibuligera* IFO 0107 (IFO means a stock strain conserved in the Institute for Fermentation, Osaka) was inoculated into the above-mentioned medium and cultured therein at 28° C. and 300 rpm under shaking.

On the third and seventh days of the culture, 0.5-g portions of a 50% by weight aqueous solution of glucose were added to the medium and the culture was continued until the 12th day.

The amount of the mevalonic acid thus produced in the culture medium determined by the method described above was 14.1 mg/ml.

COMPARATIVE EXAMPLES 1 to 5

The procedure of Example 1 was repeated except that the peptone originating from casein was replaced by those listed in Table 1. Then the amount of the mevalonic acid produced in the culture medium was similarly determined. Table 1 shows the results.

TABLE 1

| Comp. Ex. | Source of peptone | Mevalonic acid (mg/ml) |
|---|---|---|
| 1 | animal tissue | 4.3 |
| 2 | gelatin | 3.4 |
| 3 | rice | 2.9 |

TABLE 1-continued

| Comp Ex. | Source of peptone | Mevalonic acid (mg/ml) |
|---|---|---|
| 4 | cotton seed | 6.6 |
| 5 | soybean protein | 5.5 |

Note. Each peptone is a product of Oriental Yeast Co., Ltd.

COMPARATIVE EXAMPLE 6

The procedure of Example 1 was repeated except that 1.0% by weight of the corn steep liquor was replaced by 0.25% by weight of yeast extract (a product of Difco Laboratories, Inc.). Thus 12.1 mg/ml of mevalonic acid was produced in the medium.

COMPARATIVE EXAMPLES 7 and 8

The procedure of Example 1 was repeated except that no corn steep liquor was employed while not 0.5% by weight but 1.0% by weight of the peptone originating from casein was used (Comparative Example 7); or that no peptone originating from casein was used while not 1.0% by weight but 2.0% by weight of the corn steep liquor was used (Comparative Example 8). As a result, 0.7 mg/ml (Comparative Example 7) and 11.4 mg/ml (Comparative Example 8) of mevalonic acid was produced.

What is claimed is:

1. A process for the production of mevalonic acid comprising culturing, in a nutrient medium, a mevalonic acid-producing strain of *Saccharomycopsis fibuligera* having all the identifying characteristics of *Saccharomycopsis fibuligera* IFO 0107, wherein said medium contains as organic nitrogen sources, casein-derived peptone in an amount of 0.01 to 10% on a dry weight basis and corn steep liquor in an amount of 0.01 to 10% on a dry weight basis, and recovering said mevalonic acid from the medium.

2. The process for the production of mevalonic acid as claimed in claim 1, wherein the total amount of said peptone and said corn steep liquor is 0.2 to 11% by weight.

3. The process for the production of mevalonic acid as claimed in claim 2, wherein said total amount is 0.4 to 5% by weight.

4. The process for the production of mevalonic acid as claimed in claim 1, wherein said peptone has a ratio of amino nitrogen to total nitrogen of 0.20–0.40.

5. The process for the production of mevalonic acid as claimed in claim 4, wherein said ratio is 0.25–0.35.

* * * * *